United States Patent
Winkler et al.

(10) Patent No.: US 6,510,389 B1
(45) Date of Patent: Jan. 21, 2003

(54) ACOUSTIC DETECTION OF STRESS-INDUCED MECHANICAL DAMAGE IN A BOREHOLE WALL

(75) Inventors: Kenneth W. Winkler, Ridgefield, CT (US); Thomas J. Plona, New Milford, CT (US); Bikash Sinha, West Redding, CT (US); Ralph M. D'Angelo, New Fairfield, CT (US); Lawrence McGowan, Danbury, CT (US)

(73) Assignee: Schlumberger Technology Corporation, Ridgefield, CT (US)

( * ) Notice: Subject to any disclaimer, the term of this patent is extended or adjusted under 35 U.S.C. 154(b) by 0 days.

(21) Appl. No.: 09/513,602

(22) Filed: Feb. 25, 2000

(51) Int. Cl.[7] ............................................... G01V 1/28
(52) U.S. Cl. ................................. 702/6; 703/5; 367/27
(58) Field of Search ................................. 702/6, 14, 16; 73/152.01; 367/31, 86; 181/104

(56) References Cited

U.S. PATENT DOCUMENTS

| | | | |
|---|---|---|---|
| 3,724,589 A | 4/1973 | Chapman, III | 181/0.5 BI |
| 3,859,851 A | 1/1975 | Urbanosky | 73/155 |
| 4,293,934 A | 10/1981 | Herolz et al. | 367/27 |
| 4,468,623 A | 8/1984 | Gianzero et al. | 324/367 |
| 4,641,724 A * | 2/1987 | Chow et al. | 181/104 |
| 4,861,581 A | 8/1989 | Zimmerman et al. | 73/155 |
| 4,936,139 A | 6/1990 | Zimmerman et al. | 73/155 |
| 5,463,320 A | 10/1995 | Bonner et al. | 324/366 |
| 5,544,127 A | 8/1996 | Winkler | 367/27 |
| 5,594,706 A | 1/1997 | Shenoy et al. | 367/78 |
| 5,808,963 A * | 9/1998 | Esmersoy | 367/31 |
| 6,098,021 A * | 8/2000 | Tang et al. | 702/14 |
| 6,351,991 B1 * | 3/2002 | Sinha | 73/152.01 |

OTHER PUBLICATIONS

Plona, T.J. et al. *Measurement of Stress Direction and Mechanical Damage Around Stressed Boreholes Using Dipole and Microsonic Techniques.* SPE/ISRM XP–002160559. vol. 1 (1998) pp. 123–129.

Anderson, Don L. et al. *The Effect of Oriented Cracks on Seismic Velocities.* Journal of Geophysical Research. vol. 79, No. 26 (Sep. 10, 1974) pp. 4011–4015.

Nur, Amos. *Effects of Stress on Velocity Anisotrophy in Rocks with Cracks.* Journal of Geophysical Research. vol. 76, No. 8 (Mar. 10, 1971) pp. 2022–2034.

Winkler, Kenneth W. *Azimuthal Velocity Variations Caused by Borehole Stress Concentrations.* Journal of Geophysical Research. vol. 101, No. B4 (Apr. 10, 1996) pp. 8615–8621.

Winkler, Kenneth W. *Acoustic Evidence of Mechanical Damage Surrounding Stressed Boreholes.* Geophysics. vol. 62, No. 1 (Jan.–Feb. 1977) pp. 16–22.

* cited by examiner

Primary Examiner—Edward Lefkowitz
Assistant Examiner—Victor J. Taylor
(74) Attorney, Agent, or Firm—John L. Lee; William B. Batzer; John J. Ryberg (57) ABSTRACT

A method provides for locating and measuring mechanical damage in rock surrounding a borehole by detecting one or both of reductions in ultrasonic compressional wave velocity in the rock as a function of azimuth, and by detecting focused acoustic energy in the rock from local increases in ultrasonic compressional wave amplitude resulting from velocity gradients. A first preferred embodiment uses a combination of azimuthal ultrasonic compressional wave velocity data and azimuthal ultrasonic compressional wave energy data. A second embodiment uses azimuthal ultrasonic compressional wave velocity data and omni-directional sonic velocity data, with a comparison test or a curve fitting test. A third embodiment uses azimuthal ultrasonic compressional wave energy data.

17 Claims, 11 Drawing Sheets

------- CONVENTIONAL SONIC

——— AZIMUTHAL ULTRASONIC

FIG.8A

ANISOTROPIC STRESSES;
DAMAGE BEGINNING

------- CONVENTIONAL SONIC

——— AZIMUTHAL ULTRASONIC

FIG.8B

ANISOTROPIC STRESSES;
DAMAGE EVERYWHERE

------- CONVENTIONAL SONIC

——— AZIMUTHAL ULTRASONIC

ACOUSTIC DETECTION OF STRESS-INDUCED MECHANICAL DAMAGE IN A BOREHOLE WALL

This application is a non-provisional application which claims priority to co-pending non-provisional application Ser. No. 09/434,694, filed Nov. 5, 1999.

FIELD OF THE INVENTION

This invention relates broadly to methods and tools for measuring formation geomechanical parameters as a function of both depth and azimuth, whereby features of the formation are determined.

BACKGROUND OF THE INVENTION

Acoustic measurements can be used to detect the presence of mechanically damaged rock in stressed rock around boreholes prior to the collapse of the borehole.

The art of sonic well logging for use in determining formation parameters is a well established art. Sonic well logs are typically derived from sonic tools suspended in a mud-filled borehole by a cable. The tools typically include a sonic source (transmitter) and a plurality of receivers which are spaced apart by several inches or feet. Typically, a sonic signal is transmitted from the transmitter at one longitudinal end of the tool and received by the receivers at the other, and measurements are made every few inches as the tool is drawn up the borehole. The sonic signal from the transmitter or source enters the formation adjacent the borehole, and the arrival times of the compressional (P-wave), shear (S-wave) and Stoneley (tube) waves are detected by the receivers. The receiver responses are typically processed in order to provide a time to depth conversion capability for seismic studies as well as for providing the determinations of formations parameters such as porosity. It has long been known that the drilling of a borehole into a formation disturbs the stress field that was present in the formation prior to the existence of the borehole. The drilling of the borehole results in circumferential and radial stress concentrations around the borehole, where the resulting stress field is strongly anisotropic at the borehole wall, but the effects of the borehole decrease rapidly with distance into the formation. It has also been established that acoustic velocities in rock are sensitive to applied stress, with both compressional and shear velocities increasing with hydrostatic stress. Uniaxial stress produces compressional and shear wave anisotropy and shear wave birefringence (velocity dependent on polarization). These results have been related by A. Nur, "Effects of Stress on Velocity Anisotropy in Rocks with Cracks", Journal Geophysics. Res.; Vol. 76, 8, p. 2022(1971), and by D. L. Anderson et al., "The Effect of Oriented Cracks on Seismic Velocities", Journal Geophysics Res.; Vol. 82 p.5374 (1974), to stress-induced anisotropy of microcrack orientations. U.S. Pat. No. 5,544,127, issued Aug. 6, 1996, to Winkler, a co-inventor of the present invention, discloses the use of a sonic borehole tool to measure velocity around the borehole as a function of azimuth. In this patent Winkler teaches that formation properties can be determined from a knowledge of velocity as a function of azimuth, and that the azimuthal direction of minimum velocity around the borehole predicts the propagation direction of artifically induced hydrofractures. He further teaches that sonic velocity variation around the borehole at a particular depth of the borehole may be taken as an indication of susceptibility to failure, with higher velocity variations indicative of a more poorly consolidated formation or a formation with a large uniaxial stress. He further teaches that the curvature of the velocity versus stress curve in the formation is indicated by how poorly a sine wave fits to the velocity data. He further teaches that other parameters of the formation may be obtained by fitting a best fit curve to the azimuth versus velocity data, where adjustable parameters of the best fit curve constitute the formation parameters.

Acoustic measurements are better able to detect mechanical damage than are other logging techniques based on resistivity, density, radioactivity, or magnetic resonance because the acoustic waves stress and strain the solid granular structure of the rock.

SUMMARY OF THE INVENTION

The invention provides a method for locating and measuring mechanical damage in rock surrounding a borehole by using one or both of reductions in ultrasonic compressional wave velocity in the rock as a function of azimuth, and increase in focused acoustic energy in the rock associated with local increase in ultrasonic compressional wave amplitude resulting from velocity gradients. A first preferred embodiment uses a combination of azimuthal ultrasonic compressional wave velocity data and azimuthal ultrasonic compressional wave energy data. A second embodiment uses azimuthal ultrasonic compressional wave velocity data and omni-directional sonic velocity data, with a comparison test or a curve fitting test. A third embodiment uses azimuthal ultrasonic compressional wave energy data.

DETAILED DESCRIPTION OF THE INVENTION

Figure 1:
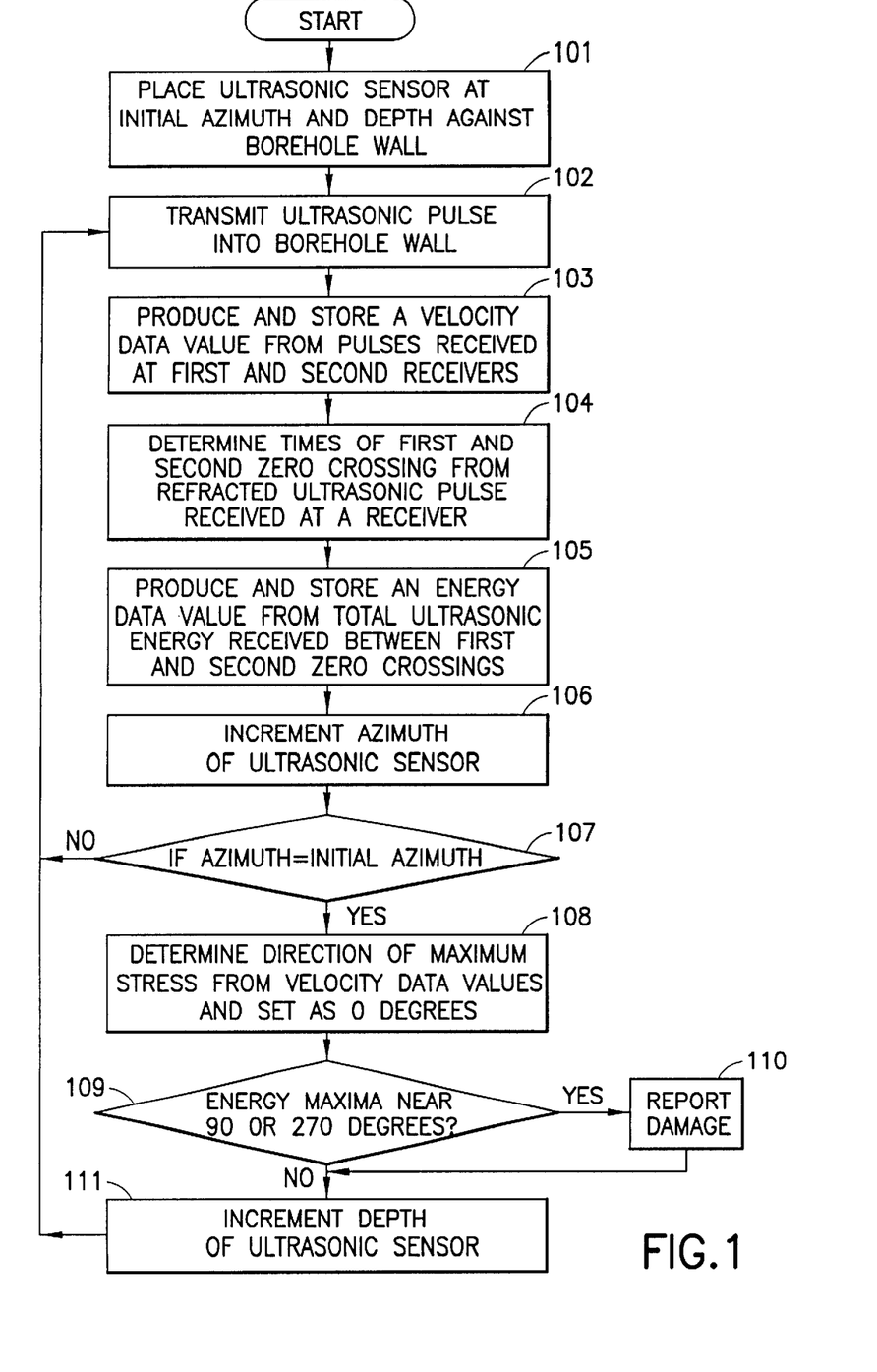
FIG. 1 is a flowchart of a first preferred embodiment of the method of the invention.

A first preferred embodiment of a method according to the present invention is shown in the flowchart of FIG. 1. The first preferred embodiment uses a combination of azimuthal ultrasonic compressional wave velocity information and azimuthal ultrasonic compressional wave amplitude information to locate and measure mechanical damage in the rock, using pulses of waves having frequencies above 25 kHz.

Figure 2:
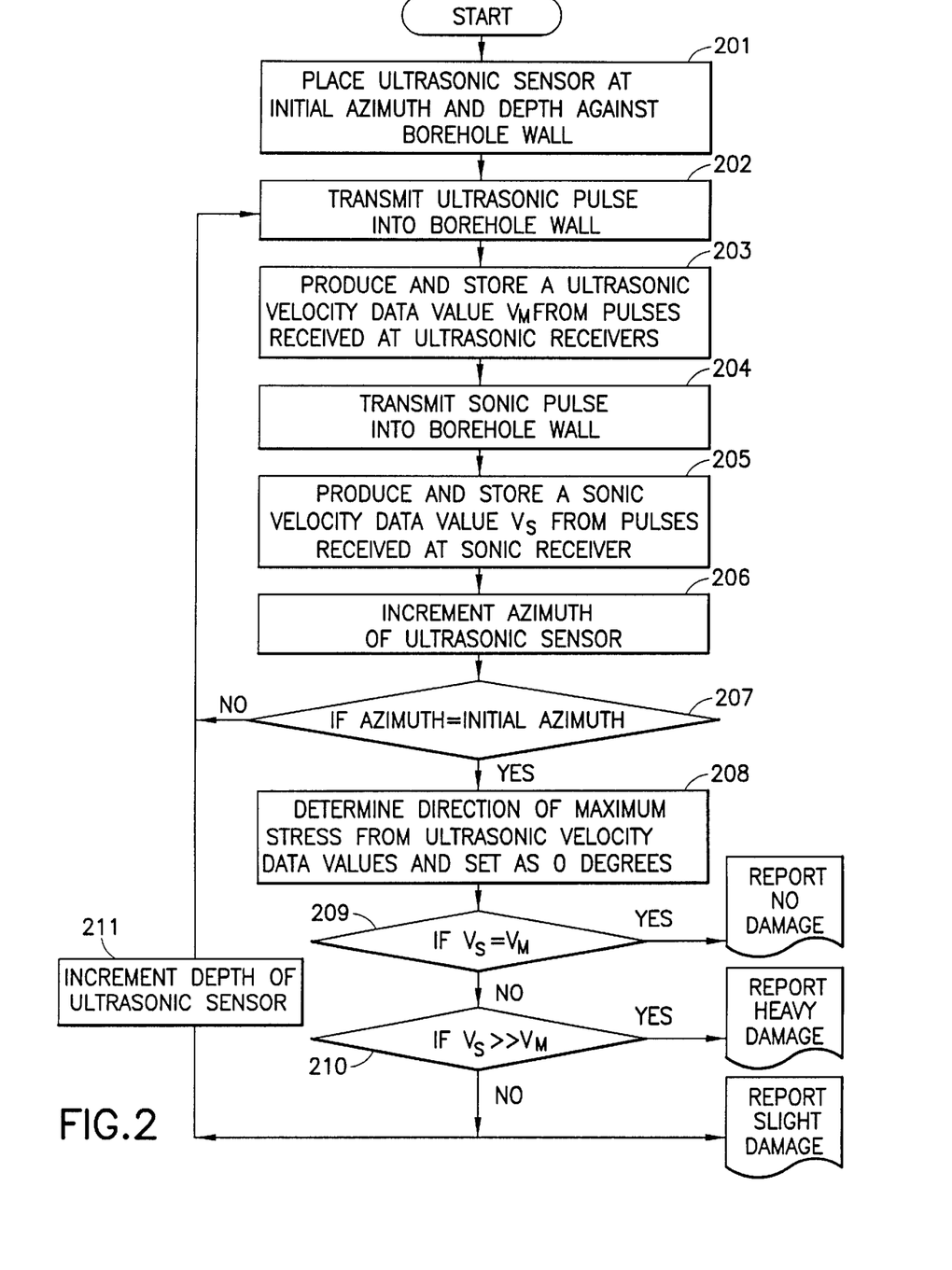
FIG. 2 is a flowchart of a second embodiment of the method of the invention.

A second embodiment of a method according to the invention is shown in the flowchart of FIG. 2. The second embodiment uses a comparison of azimuthal ultrasonic compressional wave velocity and omni-directional sonic velocity to locate and measure mechanical damage in the rock.

Figure 3:
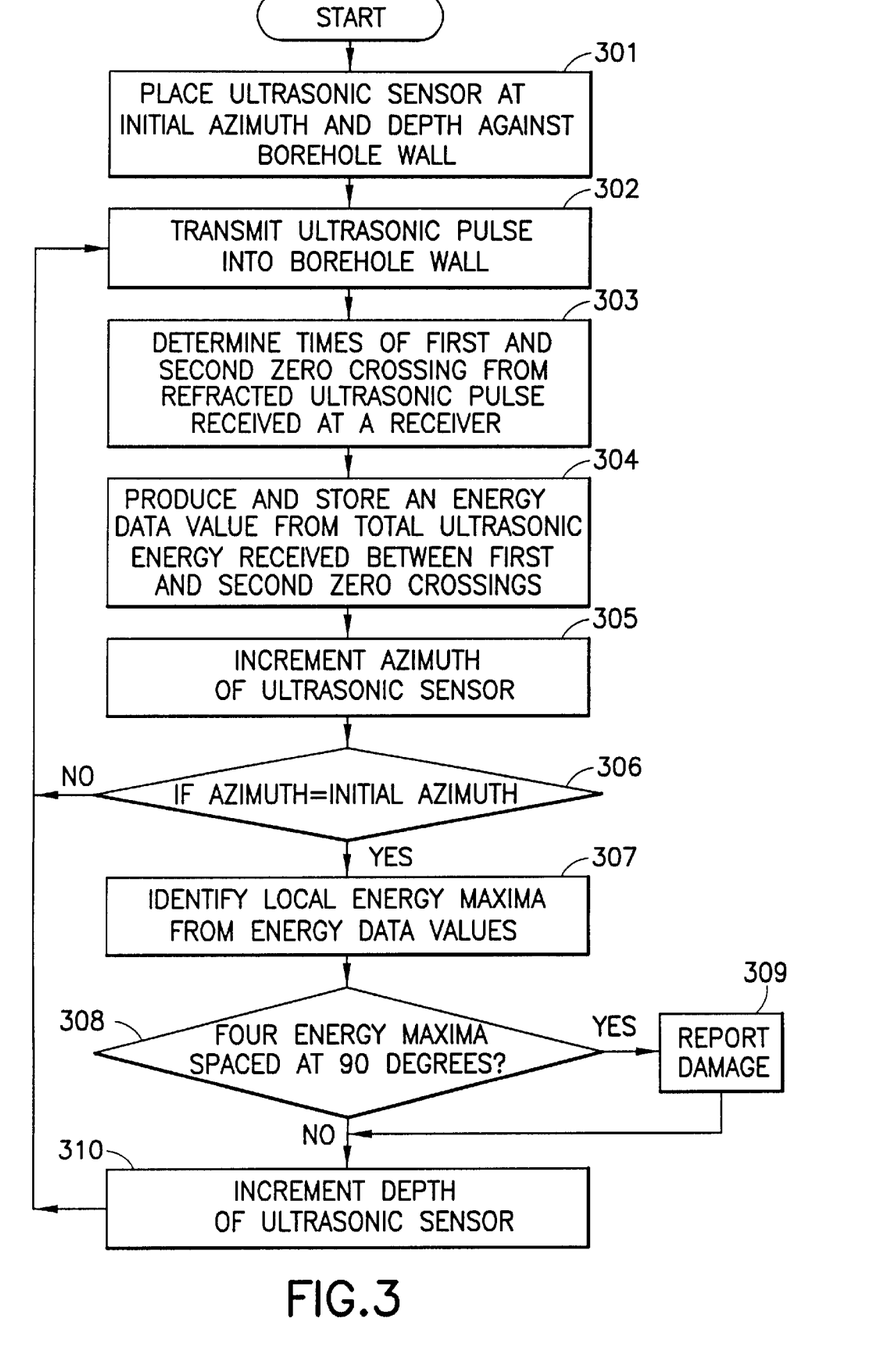
FIG. 3 is a flowchart of a third embodiment of the method of the invention.

A third embodiment of a method according to the invention is shown in the flowchart of FIG. 3. The third embodiment uses azimuthal ultrasonic compressional wave amplitude information to measure mechanical damage in the rock.

The method of the present invention may use a wireline tool for imaging a borehole wall, or an LWD ultrasonic tool. Suitable versions of these tools are described in co-pending U.S. application Ser. No. 09/434,694, filed Nov. 5, 1999, which is hereby incorporated herein by reference. U.S. Pat. No. 5,544,127, issued Aug. 6, 1996, to Winkler, a co-inventor of the present invention, is also hereby incorporated herein by reference.

Figure 4:
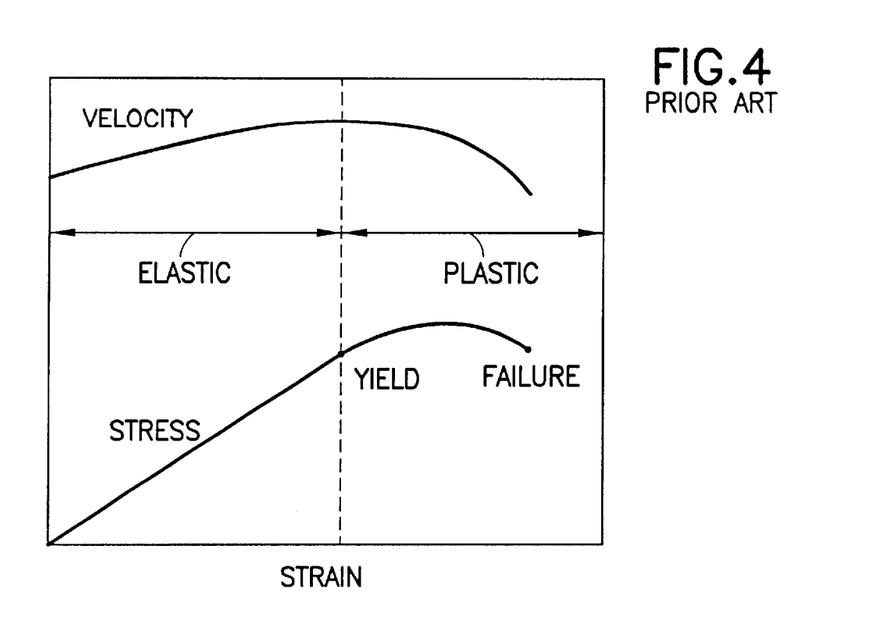
FIG. 4 is a schematic showing how velocity and stress vary with strain in a rock.

It is known that the development of mechanical damage in rocks produces a corresponding decrease in acoustic velocities. FIG. 4 shows how both velocity and stress vary with strain in a rock. At small strains the rock is in the elastic regime (below the yield point), strain is linearly proportional to stress, and acoustic velocities increase with strain. At higher strains the rock enters a plastic regime (beyond the yield point) where velocities decrease with increasing strain. Micro-mechanical damage to the rock creates plastic strain and causes velocities to decrease.

Figure 5:
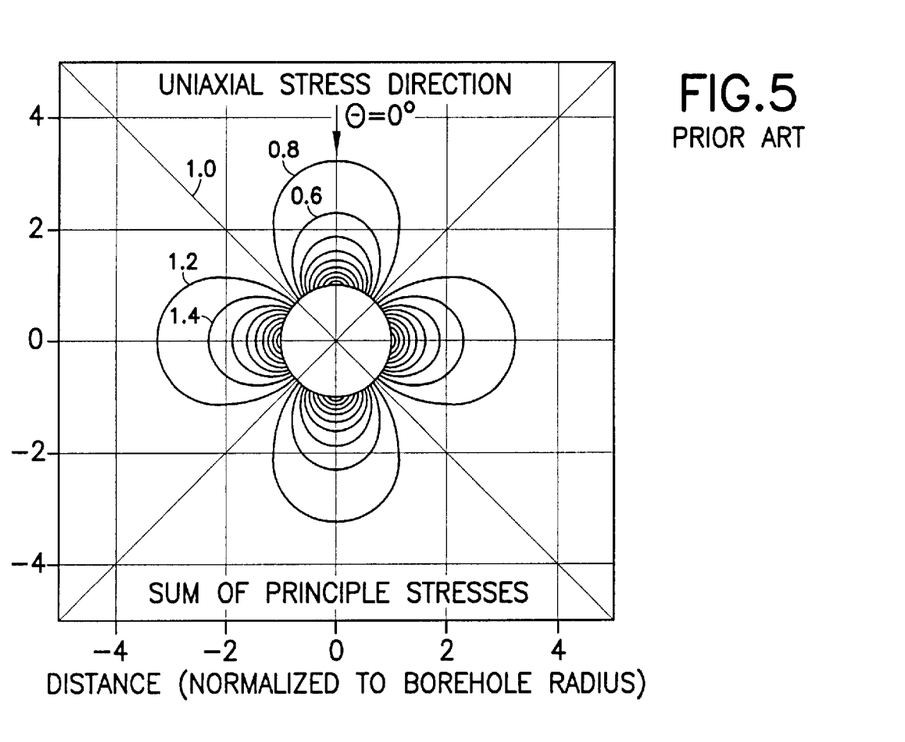
FIG. 5 is a graph showing the sum of principal stresses resulting from a unit uniaxial stress applied perpendicular to a borehole.

It is also known that stress concentrations surrounding a borehole can create plastic strain in rock. FIG. 5 shows the stress contours resulting from a uniaxial stress applied perpendicular to the borehole axis. The direction θ defines the 0° axis. Dotted contours near the borehole at 0° and 180° indicates tensile stress. Large stress concentrations near the borehole at 90 degrees and 270 degrees can exceed the yield point of the rock. When plastic strain increases sufficiently at these locations, the rock fails mechanically. Initially, this damage is evidenced by borehole breakouts at 90 degrees and 270 degrees. In extreme cases the entire borehole can collapse into itself, resulting in stuck drill pipe or a lost well.

The inventors recognized that when the yield strength of rock is exceeded near the borehole, and the acoustic velocity field surrounding the borehole reflects the resulting mechanical damage, low-velocity channels will form along the wall of the borehole at 90 and 270 degrees to the direction of externally applied stress.

The inventors further recognized that these low velocities could be measured using high-frequency, azimuthally resolved refracted acoustic waves generated and detected in the borehole.

The inventors further recognized that these low-velocity channels will refract acoustic energy back towards the borehole and create large amplitude events, or "bright-spots", in the received waveforms.

Laboratory experiments show that acoustic measurements in stressed boreholes can detect the presence of mechanically damaged rock prior to the collapse of the borehole. These acoustic indicators also occur prior to the formation of borehole breakouts, which are a conventional indicator of damaged rock. The inventors identified two acoustic damage indicators: velocities and amplitudes. Mechanical damage causes velocities in rock to decrease relative to undamaged rock. Such velocity decreases can be observed by making velocity measurements as a function of azimuth and/or radius. These velocity reductions create velocity gradients near the wellbore. These gradients can focus acoustic energy, resulting in amplitude increases. The inventors further recognized that the most reliable damage indicator would likely be a combination of both velocity and amplitude information. Variations with azimuth would distinguish stress-induced mechanical damage from chemical damage due to fluid invasion. Identification of mechanically damaged formations could aid in the optimization of drilling practices (mud weight, well trajectory) and formation completions (selective perforation, oriented perforation).

The invention provides a method for use in a wireline tool for locating and measuring mechanical damage in rock surrounding a borehole in a formation. This information may be used to determine which zones in a reservoir are prone to sanding, and to devise smart completions. For example, with such knowledge, a borehole driller using Dowell "Frac & Pack" technology could perforate only the stronger zones in a formation, and then create a hydraulic fracture into the weaker formations to minimize the need to gravel-pack.

The invention also provides a method for use in an LWD tool for locating and measuring mechanical damage in rock surrounding a borehole being drilled in a formation. This give the driller an indication of the onset of mechanical damage before serious drilling problems develop. This would enable the driller to modify his drilling procedure during the drilling process to avoid borehole stability problems.

The method of the first preferred embodiment, shown as a flowchart in FIG. 1, uses a combination of azimuthal ultrasonic compressional wave velocity information and azimuthal ultrasonic compressional wave amplitude information to locate and measure borehole wall damage. This first embodiment uses an ultrasonic tool, such as those described in the above-mentioned U.S. application Ser. No. 09/434,694, for transmitting pulses into the borehole wall and for measuring in ultrasonic compressional wave velocity at each azimuth in a portion of a borehole wall using a pair of first and second receivers to produce ultrasonic compressional wave velocity values. Also, first and second zero crossings of a compressional wave are identified, as described in U.S. patent application Ser. No. 09/434,694, and an energy value is calculated and stored. In the first preferred embodiment, the calculated energy value is the total energy between the first and second zero-crossings. It is the sum of the squared amplitude values of all the digitized waveform points between the first and second zero-crossings. A plot of such energy values will look similar to the peak amplitude vs. azimuthal position curves in FIG. 13A. The direction of maximum stress is determined in step 108 from velocity values as a function of azimuth produced and stored in step 103. The direction of maximum stress is defined as zero degrees. (Determination of the direction of maximum stress is disclosed more fully in the above-mentioned U.S. Pat. No. 5,544,127). The method of the first embodiment of the present invention involves processing the ultrasonic compressional wave velocity values and the ultrasonic compressional wave energy values to identify local energy maxima representing ultrasonic compressional wave energy focused by radial velocity gradients indicative of plastic strain in the borehole wall. Any local maxima of these curves near 90 degrees or 270 degrees (i.e. 90 degrees away from 0 degrees or 180 degrees)is indicative of damage. Larger maxima indicate greater damage. A similar procedure performed manually would involve visually inspecting raw waveform plots similar to the plots shown in FIG. 12 and looking for large amplitudes (i.e. bright spots) at 90 degrees and 270 degrees. As a variant on the first embodiment, which uses the sum of the squared amplitude values between the first two zero-crossings, other measures of the energy in the refracted wave may be used. The sum of the squared amplitude values between any two zero-crossings could be used, provided the two zero-crossings are contained within the signal of interest (either a compressional wave or a pseudo-Rayleigh wave). A less quantitative measure of energy would be to take the sum of the absolute values of the amplitude values between two zero-crossings. An even less quantitative measure of energy is the maximum absolute value of the amplitude values between two zero-crossings. This last approach does not require summation.

The method of the second embodiment, shown as a flowchart in FIG. 2, uses a comparison of azimuthal ultrasonic compressional wave velocity data and omnidirectional sonic velocity data to locate and measure mechanical damage in the rock.

The second embodiment includes recording velocity $V_M$ as a function of azimuth in step 203, and recording sonic velocity $V_S$ as a function of azimuth in step 205, and comparing $V_S$ with $V_M$ to determine whether the borehole wall has no damage, or slight damage, or heavy damage. Sonic velocity provides a measure of ultrasonic compressional wave velocity at several borehole diameters away from the borehole. Being substantially independent of azimuth, the sonic velocity curve appears as a straight line in FIGS. 8A–8C. The recording of sonic velocity is disclosed more fully in the above-mentioned U.S. Pat. No. 5,544,127. The recording of ultrasonic compressional wave velocity is disclosed more fully in the above-mentioned application Ser. No. 09/434,694.

Figure 8A:
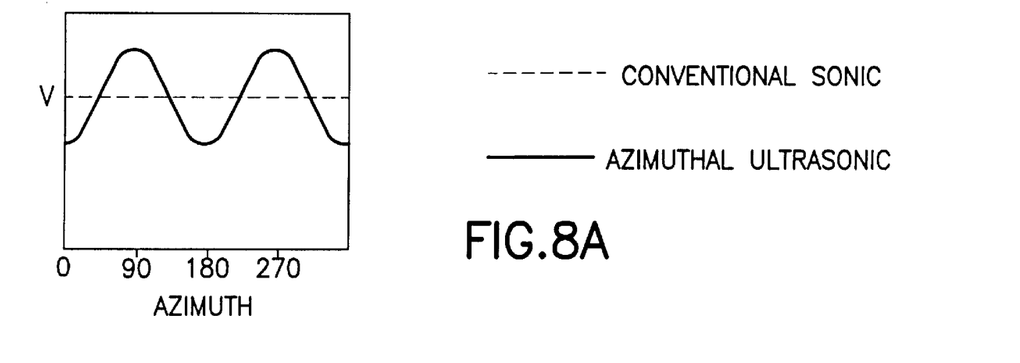
FIGS. 8A, 8B, and 8C are graphs displaying velocity vs. azimuth curves of ultrasonic compressional wave data and conventional sonic data at three different stress levels indicating three different damage levels.
Figure 8B:
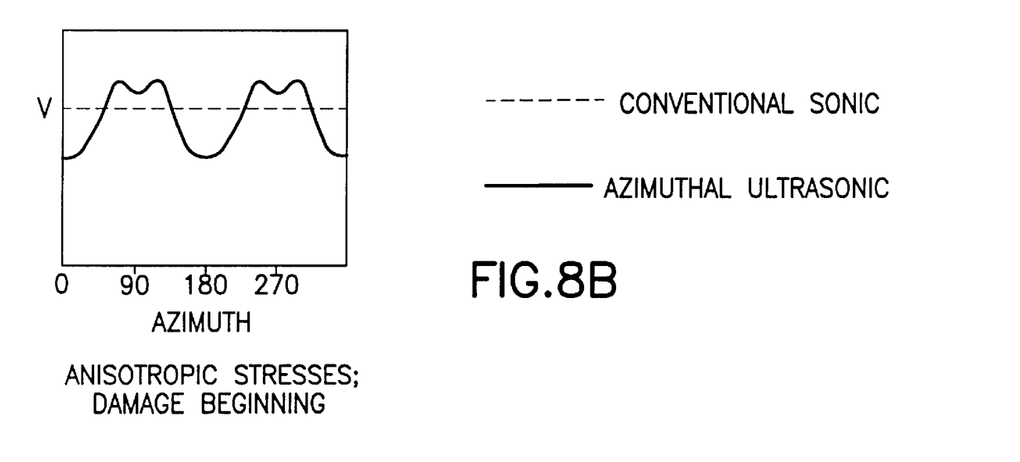
Figure 8C:
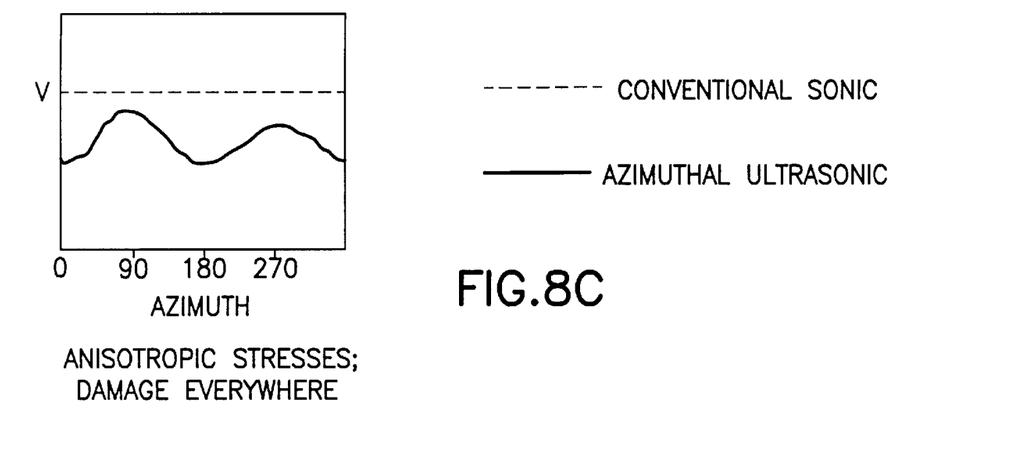

FIGS. 8A, 8B, and 8C display velocity vs. azimuth curves of ultrasonic compressional wave data and conventional sonic data at three different stress levels corresponding to low stress/($V_S=V_M$)/no damage, moderate stress/($V_S>V_M$)/ slight damage, and high stress($V_S>>V_M$)/heavy damage, respectively.

A first variant of the second embodiment includes testing the $V_M$ curve for fit with a sinusoidal waveform. A good fit indicates no damage (as illustrated in FIG. 8A). A poor fit indicates slight damage or heavy damage (FIGS. 8B and 8C).

A second variant of the second embodiment includes testing the $V_M$ curve for fit with a sinusoidal waveform, and testing for deviations towards lower velocities near the peaks of the sinusoid. Recognizable deviations indicate slight damage (compare FIG. 8B with FIGS. 8A and 8C).

A third variant of the second embodiment includes testing for ultrasonic compressional wave velocities less than the sonic velocity. Ultrasonic compressional wave velocities less than the sonic velocity at most or all azimuths indicate heavy damage (FIG. 8C).

The method of the third embodiment, shown as a flowchart in FIG. 3, uses azimuthal ultrasonic compressional wave amplitude information to locate and measure mechanical damage in the rock. Producing and storing an energy data value from total ultrasonic compressional wave energy received between first and second zero crossings (step 304) includes calculating the total energy between the first and second zero-crossings as the sum of the squared amplitude values of all the digitized waveform points between the first and second zero-crossings. The energy vs. azimuth curve, if plotted, would look similar to the amplitude vs. azimuth curves in FIG. 13A. Four energy maxima spaced at approximately 90 degrees indicate damage in the borehole wall.

A similar procedure can be performed manually by visually inspecting raw waveform plots and identifying large amplitudes (bright spots) spaced at 90 degrees, as illustrated in FIG. 12.

Experimental Data

Figure 6:
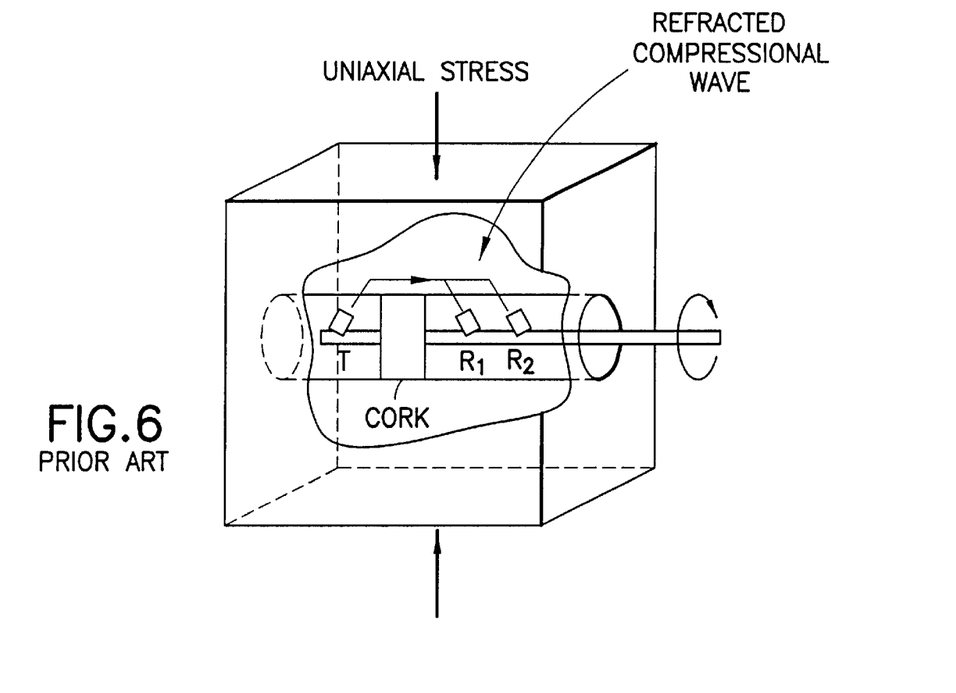
FIG. 6 is a schematic of experimental apparatus used to evaluate the method of the present invention.

FIG. 6 is a schematic of an experimental apparatus used to evaluate the method of the present invention. A block of rock with a horizontal borehole was placed inside a water tank on a uniaxial press. The press applied stress to the rock perpendicular to the borehole axis. A miniature acoustic tool for sending a directional acoustic beam into the rock over a narrow range of azimuths was inserted into the borehole. (This is in contrast to conventional sonic logging tools that insonify the formation simultaneously at all angles). The tool was rotated in 10 degree increments. At each of a series of azimuths (10 degree increments), for each of a series of uniaxial stress levels, a series of waveforms transmitted from transmitter T were recorded as received at receivers R1 and R2. The transducers were directional, not monopole, so the first arrival at the receivers was refracted through the rock at a particular azimuth. A cork plug was provided to eliminate tool arrivals and direct fluid arrivals. Velocity was computed at each of the series of azimuths for each of a series of uniaxial stress levels. Uniaxial stress on the rock was increased to create stress concentrations, breakouts, and eventual collapse of the block.

Figure 7:
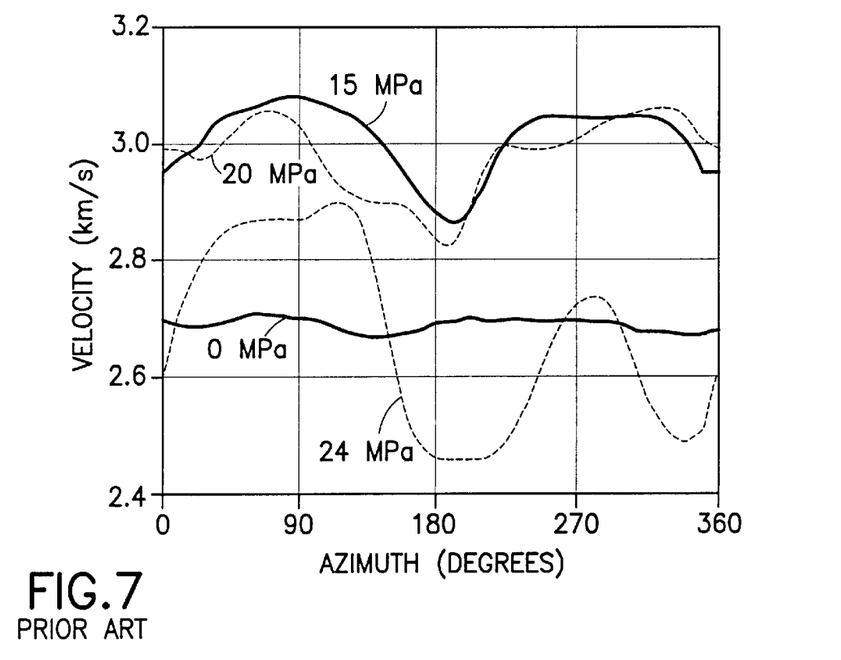
FIG. 7 is a graph of velocity against azimuth at four successively higher stress levels, from data obtained in an experiment using the apparatus of FIG. 6.

FIG. 7 is a graph displaying data obtained in an experiment using the apparatus of FIG. 6. The graph shows velocity versus azimuth in Berea sandstone at various values of external uniaxial stress. Velocity decreases at 20 MPa are evidence of mechanical damage. Increasing stress to 24 MPa further damages the rock.

At 0 MPa stress, velocity is shown as essentially independent of azimuth. At stresses up to 15 MPa, velocity is shown as a symmetric function of azimuth. Velocity maxima are shown as occuring at 90 degrees and 270 degrees, which are regions of compressive stress concentration. Velocity minima are shown as occuring at 0 degrees and 180 degrees, where stress is minimum. Although the data are not shown, increasing stress up to 15 MPa caused velocities to continuously increase. Referring to FIG. 1, this suggests that the yield point of the rock was not exceeded. As stress increased beyond 15 MPa to 20 MPa, we see at many azimuths the velocities are actually less than they were at 15 MPa. This indicates that the yield point of the rock was exceeded. At that point the rock was mechanically damaged. As stress continued to increase to 24 MPa, the velocities continued to decrease and became asymmetric with respect to azimuth. The block collapsed completely at 25 MPa.

In practice we would not have a series of ultrasonic compressional wave velocity curves as in FIG. 7, but would only have a single curve representative of the current state of stress and damage. By comparing this single curve to the velocity measured far from the borehole with conventional sonic tools, we can better gauge the state of damage surrounding the hole. This is shown schematically in FIGS. 8A–8C. FIG. 8A represents low stress where damage has not yet begun. At low uniaxial stress, the azimuthal ultrasonic compressional wave velocity varies approximately sinusoidally about the sonic velocity. The ultrasonic compressional wave velocity minima indicate the direction of maximum stress perpendicular to the borehole. FIG. 8B shows that at moderate stress, as damage begins to occur in the zones of high compressive stress, and as the rock begins to yield prior to the formation of breakouts, the ultrasonic compressional wave velocity maxima become distorted. FIG. 8C shows that at high stress, as damage progresses around the borehole, the ultrasonic compressional wave velocities at all azimuths are less than the conventional sonic velocity, and the entire ultrasonic compressional wave velocity curve can drop below the conventional sonic value, indicating significant damage all around the wellbore.

Figure 9:
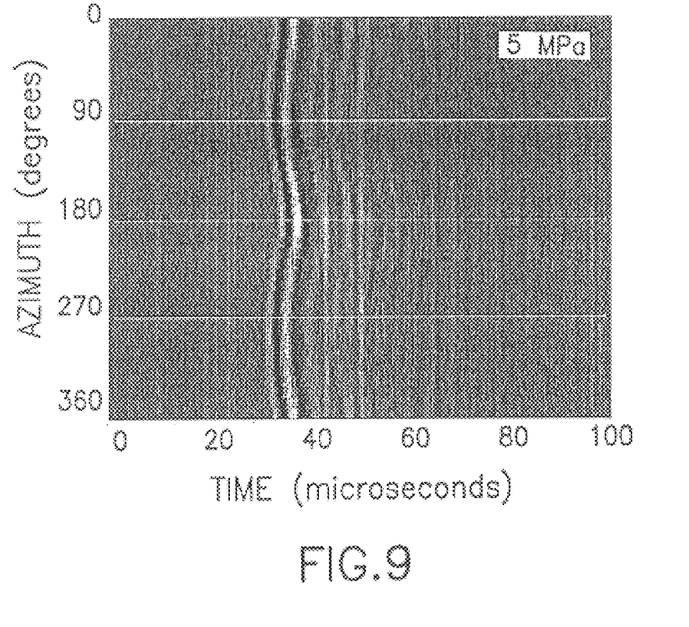
FIG. 9 is a density plot of waveforms recorded versus azimuth at 5 MPa uniaxial stress, showing bright regions at 0° and 180° caused by ray focusing induced by radial velocity gradients.

Another indication of mechanical damage can be seen in the raw waveforms recorded during these experiments. FIG. 9 shows a variable density plot of waveforms recorded at the near receiver with a uniaxial stress of 5 MPa on the rock. From the previous discussion, significant damage is not expected at this stress. The first arrival in FIG. 9 shows a sinusoidal pattern caused by the variation in velocity around the borehole. Bright regions at 0° and 180° are caused by ray focusing induced by radial velocity gradients resulting from tensile stress concentrations.

Figure 10:
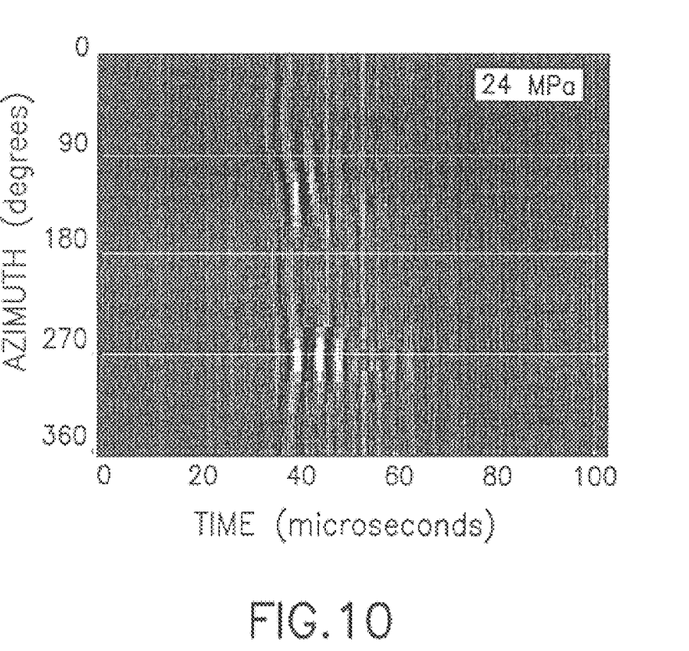
FIG. 10 is a density plot of waveforms recorded versus azimuth at 24 MPa uniaxial stress, when the rock is on the verge of failure.

FIG. 10 is a density plot of waveforms recorded versus azimuth at 24 MPa uniaxial stress, when the rock is on the verge of failure.

Figure 11A:
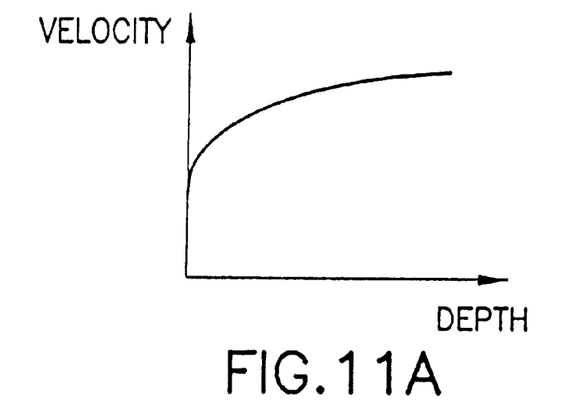
FIG. 11A is a graph showing ultrasonic compressional wave velocity increasing away from the borehole.
Figure 11B:
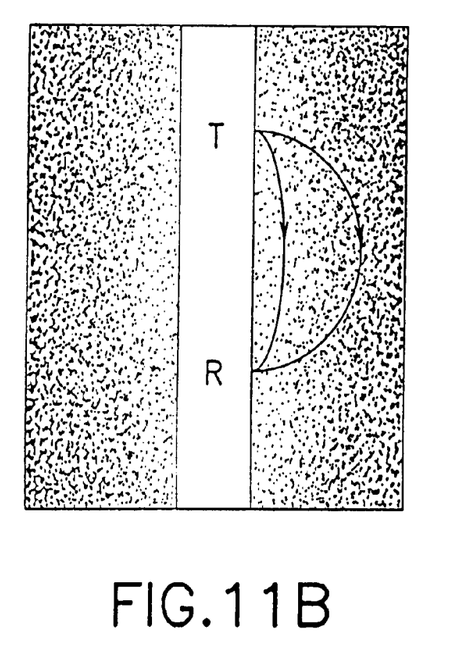
FIG. 11B is a schematic of acoustic focusing caused by the radial velocity gradients illustrated in FIG. 11A.
Figure 12A:
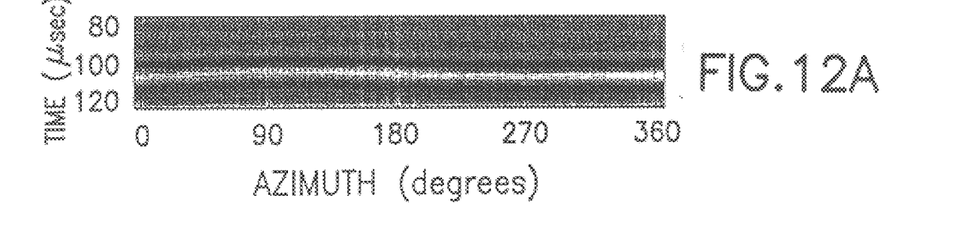
FIGS. 12A 12E are density plots showing compressional arrival as a function of time and azimuth at a fixed source-receiver spacing of 12 cm for five different stress levels from Stress Test 1: 0 Mpa; 3 Mpa; 9 MPa; 13 MPa; and 19 Mpa, respectively.
Figure 12B:
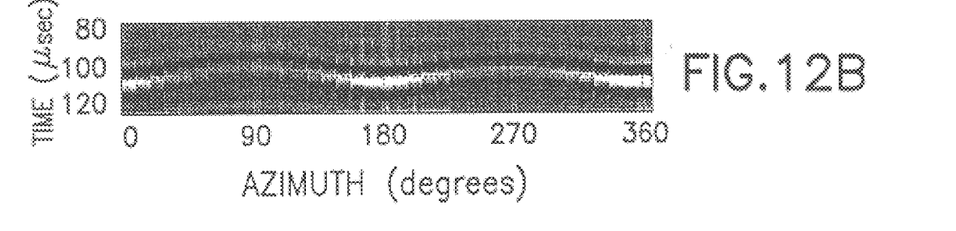
Figure 12C:
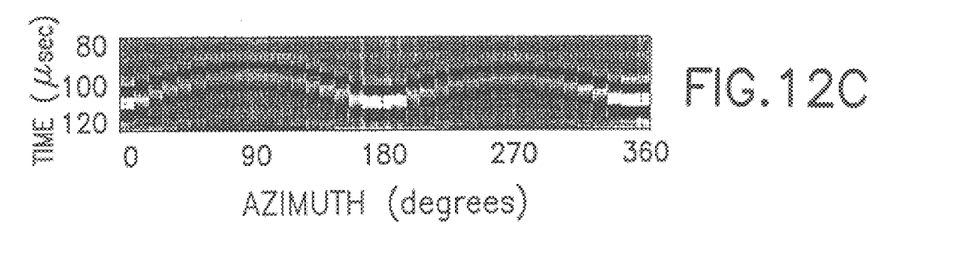
Figure 12D:
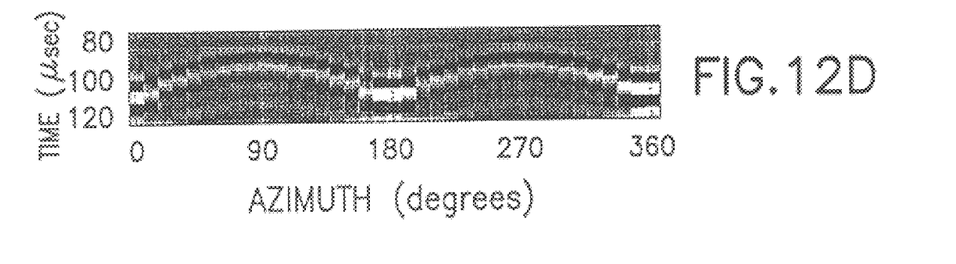
Figure 12E:
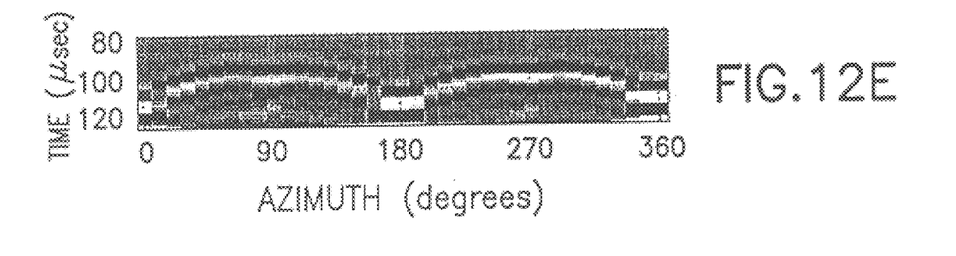

As stress increases to 24 MPa, the rock becomes mechanically damaged and the density plot changes to that shown in FIG. 10. The most significant new features are the large-amplitude events ("bright spots") which appear near 120 and 270 degrees. These are precisely the azimuths where the first indications of damage appeared in the azimuthal velocity plots (FIG. 7, 20 MPa curve). It is believed that mechanical damage at 120 degrees and 270 degrees caused by stress concentrations created low-velocity channels near the borehole wall at these azimuths. These low-velocity channels focus acoustic energy that would normally leave the borehole region and bring it back to the receiver, creating large acoustic amplitudes. Thus, bright regions of the waveforms at 120° and 270° are caused by ray focusing induced by radial velocity gradients resulting from mechanical damage. Focusing caused by radial velocity gradients is shown schematically in FIG. 11. When velocity increases with radius, deeply penetrating rays from transmitter T are refracted back to the borehole. When multiple raypaths arrive simultaneously at receiver R, and interfere constructively, a bright spot is created on a variable density plot. Similar focusing effects are commonly observed in ocean acoustics, where low-velocity layers of water trap acoustic energy and propagate it for thousands of miles through the ocean.

Density plots from another experiment are shown in FIGS. 12A–12E, where only the first arrivals are shown. Each plot is for a different value of uniaxial stress as it increased from 0, 3, 9, 13, 19 MPa. Bright spots at 0 degrees and 180 degrees are caused by low-velocity channels created by tensile stress concentrations. These are not effects of damage. Bright spots slowly develop at 90 degrees and 180 degrees, and these are indicators of damage, because this is where breakouts developed. Bright spots coincident with relatively high velocities around the borehole are indicators of mechanical damage. A low-velocity channel exists within a background of high-velocity rock, so the low-velocity channel may still have higher velocities than rock at 0 degrees and 180 degrees.

Figure 13A:
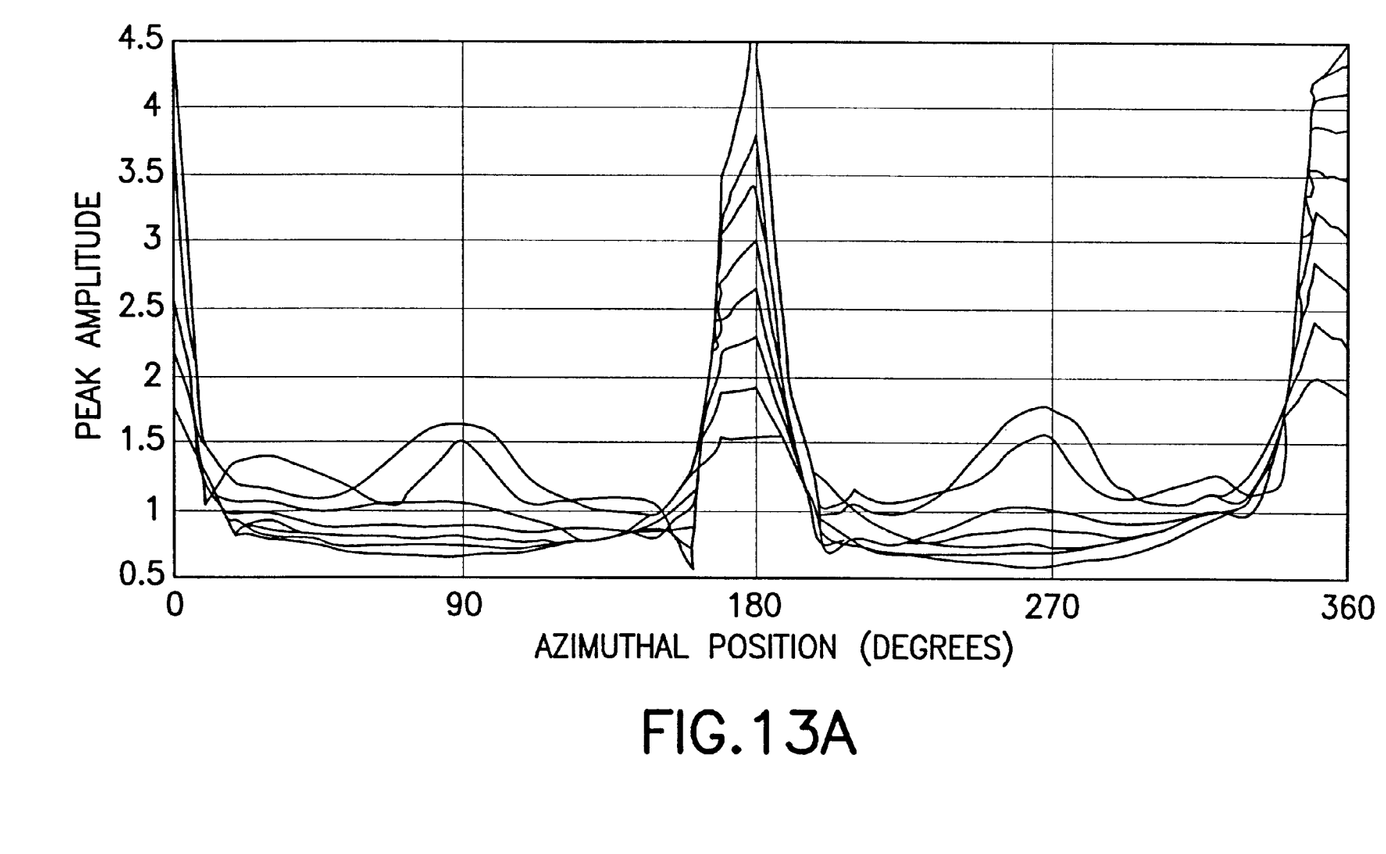
FIG. 13A is graph showing a peak amplitude of the compressional arrival as a function of azimuth for various stress levels at a source-receiver spacing of 19 cm.
Figure 13B:
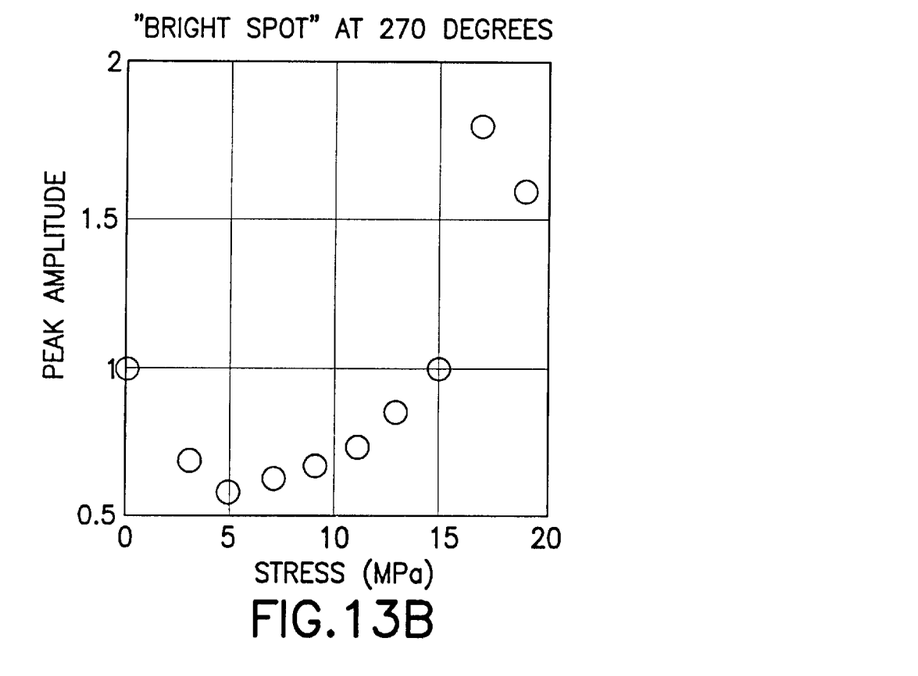
FIG. 13B is a graph of amplitude versus stress at azimuth of 270 degrees.
Figure 13C:
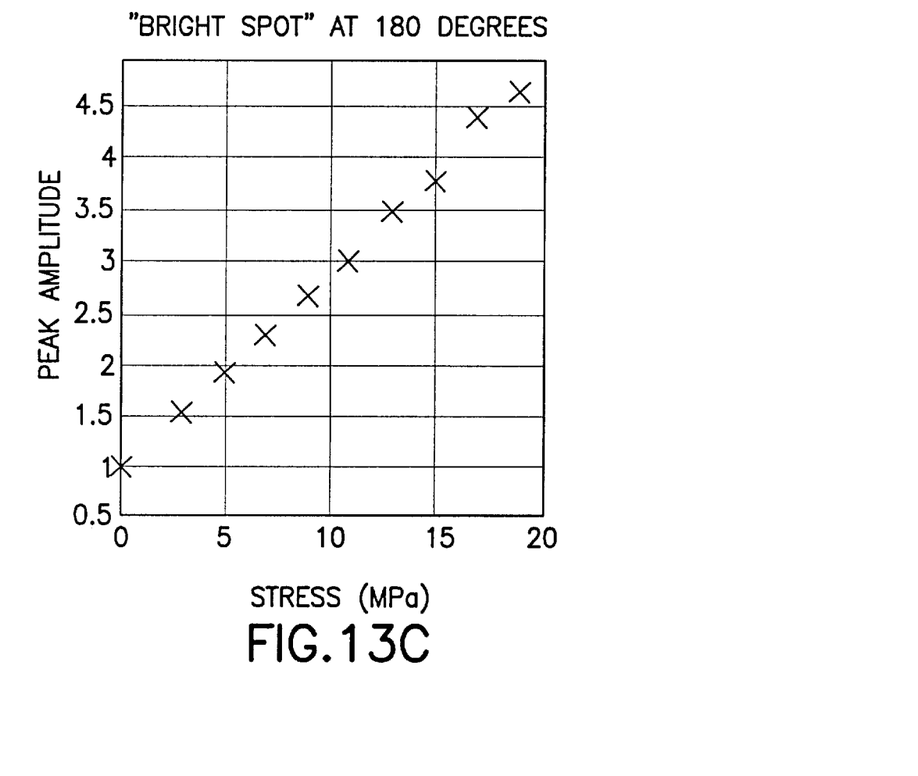
FIG. 13C is a graph of amplitude versus stress at azimuth of 180 degrees.

To quantify the information in the variable density plots of FIGS. 12A–12E, we can plot the amplitude of the first arrival as a function of azimuth, as in FIGS. 13A–13C. As uniaxial stress increases, the peaks in FIG. 13A at 0, 90, 180, and 270 degrees all increase. In this case the tensile stresses at 0 degrees and 180 degrees are more effective in creating bright spots than are the damaged zones at 90 and 270 degrees. FIG. 13B plots the peak amplitude at 180 degrees versus stress. The amplitude increases monotonically with stress, as we might expect. However, at 270 degrees, as shown in FIG. 13B, the amplitude first decreases and then increases with stress. This is consistent with explanations given above. Below 5 MPa, the rock is still in the elastic state and no damage has occurred. In that case, the radial velocity gradients at 270 degrees will be opposite to those at 180 degrees. At 270 degrees, stress and velocity will decrease with depth into the rock, so acoustic energy will actually be de-focused, or refracted away from the borehole. This causes the received amplitude to decrease. However, above 5 MPa stress, the rock begins to damage and a low-velocity channel is created. As this channel grows, more and more energy is focused back to the borehole causing the received amplitude to increase.

What is claimed is:

1. A method for locating and measuring mechanical damage in rock surrounding a borehole in a formation, the method comprising:

a) measuring ultrasonic compressional wave velocity and ultrasonic compressional wave amplitude in a portion of a borehole wall at a plurality of azimuths using pulses of waves having frequencies above 25 kHz to produce at each of the plurality of azimuths an ultrasonic compressional wave velocity value and an ultrasonic compressional wave energy value; and b) identifying at least one local energy maximum in the ultrasonic energy values.

2. A method according to claim 1, wherein measuring ultrasonic compressional wave velocity includes detecting times of zero crossings at an ultrasonic receiver.

3. A method according to claim 2, wherein times of zero crossings includes times of first and second zero crossings.

4. A method according to claim 1, wherein measuring ultrasonic compressional wave energy in a portion of a borehole wall includes summing the squared amplitudes of ultrasonic compressional wave amplitudes in a time period between zero crossings to produce ultrasonic compressional wave energy values.

5. A method according to claim 2, wherein a time period between zero crossings includes a time period between first and second zero crossings.

6. A method according to claim 1, the method further comprising:

c) identifying a direction of maximum stress; and d) defining the direction of maximum stress as 0 degrees;

wherein identifying at least one local energy maximum includes identifying local energy maxima at 90 degrees and 270 degrees.

7. A method according to claim 1, wherein measuring ultrasonic compressional wave velocity in a portion of a borehole wall includes measuring ultrasonic compressional wave velocity using a pair of first and second receivers.

8. A method for locating and measuring mechanical damage in rock surrounding a borehole in a formation, the method comprising:
   a) measuring ultrasonic compressional wave velocity using directional pulses of waves having frequencies above 25 kHz in a portion of the borehole wall at a plurality of azimuths to produce a set of ultrasonic compressional wave velocity values;
   b) measuring sonic velocity in the formation beyond the borehole wall using omni-directional sonic waves to produce a velocity value; and
   c) comparing the set of ultrasonic compressional wave velocity values with the sonic velocity value.

9. A method according to claim 8, wherein comparing the set of ultrasonic compressional wave velocity values with the sonic velocity value includes testing for average ultrasonic compressional wave velocity value equals sonic velocity value, indicative of low stress and no damage.

10. A method according to claim 8, wherein comparing the set of ultrasonic compressional wave velocity values with the sonic velocity value includes testing for average ultrasonic compressional wave velocity value greater than sonic velocity value, indicative of moderate stress and slight damage.

11. A method according to claim 8, wherein comparing the set of ultrasonic compressional wave velocity values with the sonic velocity value includes testing for average ultrasonic compressional wave velocity value much greater than sonic velocity value, indicative of high stress and heavy damage.

12. A method for locating and measuring mechanical damage in rock surrounding a borehole in a formation, the method comprising:
   a) measuring ultrasonic compressional wave velocity using directional pulses of waves having frequencies above 25 kHz in a portion of the borehole wall at a plurality of azimuths to produce a set of ultrasonic compressional wave velocity values;
   b) curve fitting the set of ultrasonic compressional wave velocity values with a sine wave; and
   c) testing the curve fit for indication of damage.

13. A method according to claim 12, wherein a good fit indicates no damage, and a finding of at least one peak of ultrasonic compressional wave velocity values below a corresponding peak of the sine wave indicates damage.

14. A method according to claim 12, wherein testing curve fit includes testing for velocities asymmetric with respect to the sine wave.

15. A method according to claim 12, further comprising:
   d) measuring sonic velocity in the formation beyond the borehole wall using omni-directional sonic waves to produce a set of sonic velocity values; and
   e) testing for ultrasonic compressional wave velocities less than the sonic velocities at most azimuths as indication of damage.

16. A method for locating and measuring mechanical damage in rock surrounding a borehole in a formation, the method comprising:
   a) measuring ultrasonic compressional wave energy amplitude of waves having frequencies above 25 kHz in a portion of a borehole wall at a plurality of azimuths to produce at each of the plurality of azimuths an ultrasonic compressional wave energy amplitude value; and
   b) identifying pairs of amplitude maxima spaced at approximately 90 degrees as indication of damage.

17. A method according to claim 16, further comprising:
   c) identifying a direction of maximum stress;
   d) defining the direction of maximum stress at 0 degrees; and
   e) locating damage at 0 degrees.

* * * * *